United States Patent [19]

Conrad et al.

[11] Patent Number: 4,457,944

[45] Date of Patent: Jul. 3, 1984

[54] 1,3-DIALKYL-CYCLOHEXANES, METHOD OF PRODUCTION AND METHOD OF USE IN COSMETICS

[75] Inventors: Jens Conrad, Hilden; Ulf-Armin Schaper; Ulrich Zeidler, both of Düsseldorf, all of Fed. Rep. of Germany

[73] Assignee: Henkel Kommanditgesellschaft auf Aktien, Düsseldorf, Fed. Rep. of Germany

[21] Appl. No.: 332,950

[22] Filed: Dec. 21, 1981

[30] Foreign Application Priority Data

Aug. 21, 1981 [DE] Fed. Rep. of Germany ....... 3133078

[51] Int. Cl.$^3$ .................. A61K 7/06; A61K 47/00
[52] U.S. Cl. .................. 424/358; 424/59; 424/63; 424/70; 424/71; 424/72; 424/168; 424/359; 424/365; 585/20
[58] Field of Search ............... 424/356, 358; 585/20

[56] References Cited

U.S. PATENT DOCUMENTS

| | | | |
|---|---|---|---|
| 3,748,231 | 7/1973 | Hosler et al. | 195/28 |
| 4,190,561 | 2/1980 | Auger et al. | 424/358 |
| 4,206,090 | 6/1980 | Schmitt | 424/358 |

OTHER PUBLICATIONS

Chem. Abs., 1967, vol. 66, p. 54730y, Mekhtien et al.
Chem. Abs., 8th Coll. Index, p. 9042s.
Chem. Abs., vol. 68, 1968, p. 1182, Babakhanov et al.
Chemical Abstracts Service Registry Handbook (1975 Supplement) Houben-Weyl Reference (p. 273) (1970).

*Primary Examiner*—Dale R. Ore
*Attorney, Agent, or Firm*—Ernest G. Szoke; Nelson Littell, Jr.

[57] ABSTRACT

A 1,3-dialkyl-cyclohexane having the formula:

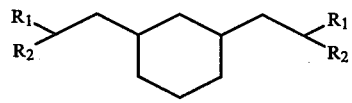

wherein $R_1$ is a member selected from the group consisting of hydrogen and straight chained or branched $C_1$–$C_{20}$-alkyl and $R_2$ is a straight chained or branched $C_1$–$C_{20}$-alkyl; as well as a method of production and its use in cosmetic preparations.

4 Claims, No Drawings

1,3-DIALKYL-CYCLOHEXANES, METHOD OF PRODUCTION AND METHOD OF USE IN COSMETICS

BACKGROUND OF THE INVENTION

The present invention relates to 1,3-dialkylcyclohexanes having the Formula I:

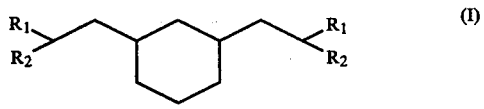

wherein $R_1$ is hydrogen or straight chained or branched $C_1$-$C_{20}$-alkyl and $R_2$ is a straight chained or branched $C_1$-$C_{20}$-alkyl; their production from the correspondingly substituted cyclohexanol or cyclohexanone compounds, and their use as a cosmetic oil, as well as products containing these compounds for the care and treatment of the face, body or hair style.

2,6-Dialkyl-cyclohexanols and methods for their production have been described, Schaper, Fette, Seifen Anstrichmittel (1980), 82, pages 454–456. With this point of departure, the previously unknown 1,3-dialkyl cyclohexane compounds were produced, and it was found, surprisingly, that these constitute especially good cosmetic oils, which can be processed excellently, for example, to colorless emulsions and smooth creams for cosmetic purposes.

OBJECTS OF THE INVENTION

It is the object of the present invention to make available new compounds for use in cosmetic products and a method for their production.

Another object of the present invention is the obtaining of a 1,3-dialkyl-cyclohexane having the formula:

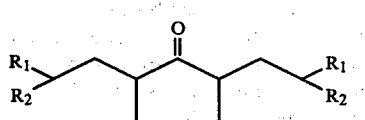

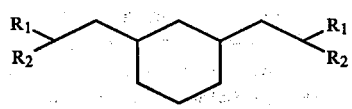

wherein $R_1$ is a member selected from the group consisting of hydrogen and straight chained or branched $C_1$-$C_{20}$-alkyl and $R_2$ is a straight chained or branched $C_1$-$C_{20}$-alkyl.

A further object of the present invention is the development of a process for the production of the above 1,3-dialkyl-cyclohexane consisting essentially of the steps of hydrogenating a compound selected from the group consisting of:

(1) 2,6-dialkyl-cyclohexanone having the formula:

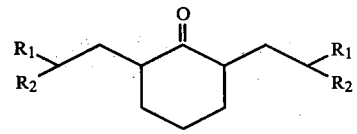

and (2) 2,6-dialkyl-cyclohexanol having the formula:

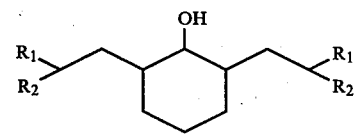

wherein $R_1$ is a member selected from the group consisting of hydrogen and straight chained or branched $C_1$-$C_{20}$-alkyl and $R_2$ is a straight chained or branched $C_1$-$C_{20}$-alkyl,
in the presence of a hydrogenation catalyst at a temperature of from 200° to 300° C. and a hydrogen pressure of between 10 and 300 bar, and recovering 1,3-dialkyl-cyclohexane.

A yet further object of the present invention is the obtaining of a cosmetic product having an effective amount of at least one 1,3-dialkyl-cyclohexane therein, together with the customary cosmetic adjuvants and auxiliaries.

These and other objects of the invention will become more apparent as the description thereof proceeds.

DESCRIPTION OF THE INVENTION

The above objects have been achieved by the development of 1,3-dialkyl-cyclohexanes which can be represented by the following general Formula I:

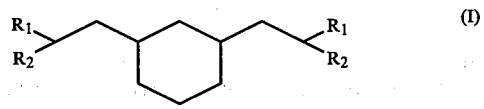

wherein $R_1$ stands for hydrogen or a possibly branched $C_1$-$C_{20}$-alkyl and $R_2$ for a possibly branched $C_1$-$C_{20}$-alkyl.

More particularly, the present invention relates to a 1,3-dialkyl-cyclohexane having the formula:

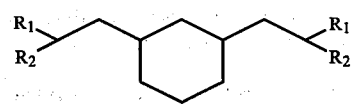

wherein $R_1$ is a member selected from the group consisting of hydrogen and straight chained or branched $C_1$-$C_{20}$-alkyl and $R_2$ is a straight chained or branched $C_1$-$C_{20}$-alkyl. Preferred are compounds in which $R_1$ and $R_2$, which may be identical or different, represent an alkyl, especially those compounds in which $R_1$ and $R_2$ stand for a $C_1$-$C_6$-alkyl, such as methyl, ethyl, propyl, butyl, pentyl or hexyl.

These compounds are prepared by a method according to the following reaction equation:

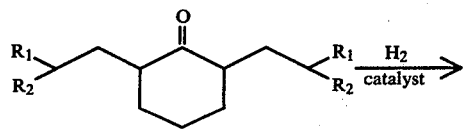

(II)

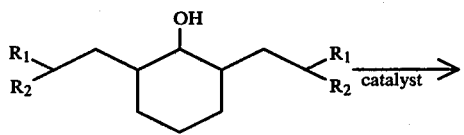

(III)

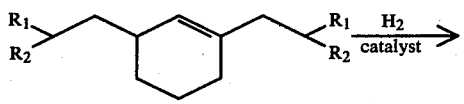

(IV)

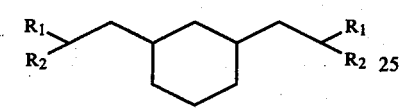

(I)

wherein $R_1$ and $R_2$ have the above-mentioned meanings.

The process of the invention of preparing the 1,3-dialkyl-cyclohexane of Formula I consisting essentially of the steps of hydrogenating a compound selected from the group consisting of:

(1) 2,6-dialkyl-cyclohexanone having the formula:

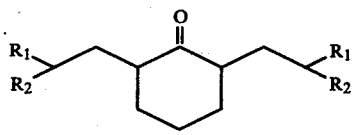

and (2) 2,6-dialkyl-cyclohexanol having the formula:

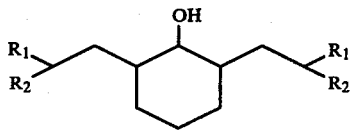

wherein $R_1$ is a member selected from the group consisting of hydrogen and straight chained or branched $C_1$–$C_{20}$-alkyl and $R_2$ is a straight chained or branched $C_1$–$C_{20}$-alkyl,
in the presence of a hydrogenation catalyst at a temperature of from 200° to 300° C. and a hydrogen pressure of between 10 and 300 bar, and recovering 1,3-dialkyl-cyclohexane.

As starting product for the production of 1,3-dialkyl-cyclohexanes of the invention, a cyclohexanone (II) or cyclohexanol (III) correspondingly substituted in the 2 and 6 positions with the desired alkyls is employed. Either are hydrogenated under hydrogenating conditions in the presence of a catalyst at elevated temperature and a hydrogen pressure of 10 to 300 bar for several hours, for example, 5 to 15 hours. All reaction steps are carried out without isolation of the respective intermediate products in the single pot method. Suitable hydrogenation catalysts are, for example, metallic nickel, cobalt, iron, or precious metals, such as platinum or palladium. Preferably the reaction is carried out with a nickel catalyst at temperatures of 200° to 300° C. The 2,6-dialkyl-cyclohexanol compounds used as starting products are obtained by mixed aldol condensation between 2 mols of aldehyde of the Formula V:

wherein $R_1$ and $R_2$ have the above-mentioned meanings, and one mol of cyclohexanone and subsequent hydrogenation. Alternatively, the 2,6-dialkyl-cyclohexanol (III) compounds can be obtained from alcohol of the Formula VI:

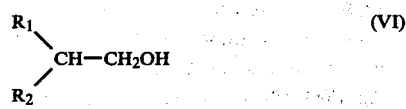

where $R_1$ and $R_2$ have the above-mentioned meaning, and cyclohexanol under the conditions of a mixed Guerbet alcohol reaction. This method for the production of 2,6-dialkyl-cyclohexanol has been described in Schaper, Fette, Seifen, Antrichmittel (1980), 82, pages 554-556.

The products according to the invention occur in the form of colorless oils. They are odorless and they are especially well suitable as cosmetic oils. They have refatting properties, and they are very well tolerated by the skin. The saturated, branched hydrocarbons used until now as an ointment base in cosmetic creams, such as Vaseline, cause heat accumulation on the skin surface as they clog the pores of the skin. This heat accumulation usually creates an unpleasant hot feeling. This undesired effect is avoided when using the compounds of the invention instead of the Vaseline. The compounds of the invention can be incorporated readily into various cosmetic preparations, such as suspensions, gels, emulsions, ointments, pastes, or shaking mixtures. Among the cosmetic products in which the compounds of the invention are usable are, for example, skin creams, body lotions, cleansing lotions, makeup bases, or sun protection agents.

In addition to the compounds according to the invention, the topical cosmetics may contain other components, such as preservatives, sequestering agents, perfumes, solvents, opacifiers, thickeners, dyes, pH-modifying additives, plant extracts, skin care ingredients, such as collagens, fatty acids, fatty acid esters, glycols, glycol ethers, animal, plant or synthetic oils and the like.

The compounds according to the invention are present in the cosmetics generally in quantities of 2% to 25% by weight, preferably 5% to 15% by weight, referred to the total weight of the cosmetic.

The following examples will further explain the present invention without being limitative in any manner. In the examples, all of the boiling points are indicated at the pressure measured in "mbars".

EXAMPLE 1

Production of 1,3-di-(2-ethylhexyl)-cyclohexane

300 Grams of 2,6-di(2-ethylhexyl)-cyclohexanol were hydrogenated with 30 gm of Girdler nickel 49A for six hours at 250° C. and 250 bar of hydrogen pressure. After filtration of the catalyst, 260 gm of 1,3-di-(2-ethylhexyl)-cyclohexane remained with the following characteristics:

| Acid number: | 0.1 |
|---|---|
| Hydroxyl number: | 0 |
| Iodine number: | 0 |
| Molar mass: | 308 (theory 308) |
| IR (oil) cm$^{-1}$: | 2965, 2930, 2880, 2865, 1460, 1380. |

EXAMPLE 2

Production of 1,3-di-(2-ethylhexyl)-cyclohexane

200 Grams of 2,6-di-(2-ethylhexyl)-cyclohexanol were hydrogenated for 13 hours at 250° C. and 20 bar of hydrogen pressure with 10 gm of a nickel catalyst containing about 22% nickel bonded on kieselguhr in a hard fat (Pricat 9904 of Unichema). After filtration of the catalyst, 171 gm of 1,3-di-(2-ethylhexyl)-cyclohexane were obtained after distillation at 0.01 mbar between 118° and 123° C.

| Characteristics: | |
|---|---|
| Acid number: | 0.2 |
| Hydroxyl number: | 1.5 |
| Iodine number: | 1.4 |
| IR (oil) cm$^{-1}$: | 2965, 2930, 2880, 2865, 1460, 1380. |

EXAMPLE 3

The same reaction of Example 2 was repeated with 20 gm of Pricat catalyst. After 15 hours hydrogenation time, 160 gm of 1,3-di-(2-ethylhexyl)-cyclohexane were obtained having the following characteristics:

| Acid number: | 0.1 |
|---|---|
| Hydroxyl number | 0 |
| Iodine number | 0.4 |
| B.P.$_{0.013}$: | 127° C. |

EXAMPLE 4

Production of 1,3-diisobutyl-cyclohexane

85 Grams of 2,6-diisobutyl-cyclohexanol were hydrogenated with 8.5 gm of Girdler nickel 49A for eight hours at 250° C. and 250 bar of hydrogen pressure. After filtration of the catalyst, 61 gm of the hydrocarbon 1,3-diisobutyl-cyclohexane were isolated by distillation.

| Characteristics: | |
|---|---|
| Acid number: | 0.1 |
| Hydroxyl number | 0 |
| Molar number: | 196 |
| Theory: | 196 |
| B.P.$_{0.07}$: | 51° C. |
| IR (oil) cm$^{-1}$: | 2960, 2930, 2865, 2845, |

| Characteristics: | |
|---|---|
| | 1470, 1385, 1370, 1170. |

EXAMPLE 5

1,3-Di-(2-ethylbutyl)-cyclohexane

As described in Example 4, starting from 94 gm of 2,6-di-(2-ethylbutyl)-cyclohexanol, 62 gm of the hydrocarbon 1,3-di-(2-ethylbutyl)-cyclohexane were produced with 9.4 gm of Girdler nickel 49A.

| Characteristics: | |
|---|---|
| Acid number: | 0 |
| Hydroxyl number: | 0.5 |
| Molar mass: | 252 |
| Theory: | 252 |
| B.P.$_{0.01}$93° to 95° C. | |
| IR (oil) cm$^{-1}$: | 2960, 2920, 2865, 2860 1460, 1380. |

EXAMPLE 6

1,3-(Di-(2-methylpentyl)-cyclohexane

As described in Example 4, starting from 100 gm of 2,6-di-(2-methylpentyl)-cyclohexanol, 75 gm of the hydrocarbon 1,3-di-(2-methylpentyl)-cyclohexane were produced with 10 gm of Girdler nickel 49A.

| Characteristics: | |
|---|---|
| Acid number: | 0 |
| Hydroxyl number: | 0 |
| Molar mass: | 252 |
| Theory | 252 |
| B.P.$_{0.01}$: | 88° to 91° C. |
| IR (oil) cm$^{-1}$: | 2965, 2930, 2870, 2850, 1468, 1455, 1380, 1155. |

EXAMPLE 7

1,3-Didecyl-cyclohexane

137 Grams of 2,6-didecyl-cyclohexanol were hydrogenated with 14 gm of Girdler nickel 49A. 71 Grams of the hydrocarbon 1,3-didecyl-cyclohexane were recovered.

| Characteristics: | |
|---|---|
| Acid number: | 0 |
| Hydroxyl number: | 0 |
| Molar mass: | 364 |
| Theory: | 364 |
| B.P.$_{0.01}$: | 174° to 180° C. |
| IR (oil) cm$^{-1}$: | 2965, 2925, 2860, 1468, 1460, 1380. |

In the following, examples for cosmetic products according to the invention are given. The oils and oil-soluble components (I) were heated to 70° to 80° C. and mixed with the aqueous phase (II) which was also heated to 70° C. by stirring. Depending on the solubility, the preservative was previously dissolved in one of the two phases. The mixture was then cooled to room temperature with constant agitation.

EXAMPLE 8

Liquid Oil in Water (O/W) Emulsion

| | | |
|---|---|---|
| (I) | Lanette O ($C_{12-18}$ fatty alcohol) | 3.5% |
| | Eumulgin B1 (cetyl/stearyl alcohol adducted with about 12 mols of ethylene oxide | 3.0% |
| | 1,3-Di-(2-ethylhexyl)-cyclohexane | 5.0% |
| (II) | 1,2-Propylene glycol | 3.0% |
| | Urea | 2.0% |
| | Water | 83.5% |

EXAMPLE 9

Oil in Water (O/W) Cream

| | | |
|---|---|---|
| (I) | Eumulgin B3 ($C_{12-18}$ fatty alcohol adducted with about 30 mols of ethylene oxide | 13.0% |
| | Cetiol HE (a $C_{12-18}$ fatty acid ester with polyols | 20.0% |
| | 1,3-Di-(2-ethylhexyl)-cyclohexane | 5.0% |
| (II) | Glycerol 86% | 20.0% |
| | Water | 42.0% |

EXAMPLE 10

Oil in Water (O/W) Hair Styling Cream

| | | |
|---|---|---|
| (I) | Eumulgin B1 | 5.0% |
| | Cutina MD (palmitic/stearic acid mono- and di-glyceride) | 15.0% |
| | 1,3-Di-(2-ethylhexyl)-cyclohexane | 20.0% |
| (II) | Water | 60.0% |

EXAMPLE 11

Oil in Water (O/W) Cleansing Cream

| | | |
|---|---|---|
| (I) | Lanette 16 (cetyl alcohol) | 2.0% |
| | Cutina MD (mixture of mono- and di-glycerides of palmitic and stearic acid) | 14.0% |
| | Eumulgin B1 (cetylstearylalcohol adducted with about 12 mols of ethylene oxide) | 1.5% |
| | Eumulgin B2 ($C_{16-18}$ - fatty alcohol adducted with about 20 mols of ethylene oxide) | 1.5% |
| | Cetiol LC (a caprylic/capric fatty acid ester with saturated $C_{12-18}$ fatty alcohols | 7.0% |
| | 1,3-Di-(2-ethylhexyl)-cyclohexane | 15.0% |
| (II) | Water | 59.0% |

EXAMPLE 12

Water in Oil (W/O) Cream

| | | |
|---|---|---|
| (I) | Dehymuls K (mixture of Dehymuls E and fatty alcohol fatty acid esters and mineral fats) | 25.0% |
| | Myritol 318 (lower boiling fatty acid glycerides) | 10.0% |
| | 1,3-Di-(2-ethylhexyl)-cyclohexane | 5.0% |
| (II) | Water | 60.0% |

EXAMPLE 13

(W/O) Cream

| | | |
|---|---|---|
| (I) | Dehymuls E (mixture of higher molecular esters, pref. pentaerithrit fatty acid ester and fatty alcohol citrate) | 8.0% |
| | Vaseline, white | 15.0% |
| | 1,3-Di-(2-ethylhexyl)-cyclohexane | 8.0% |
| (II) | Glycerol 87% | 3.0% |
| | $MgSO_4.7H_2O$ | 0.3% |
| | Water | 65.7% |

EXAMPLE 14

(W/O) Cream

| | | |
|---|---|---|
| (I) | Dehymuls E (mixture of higher molecular esters, pref. pentaerithrit fatty acid ester and fatty alcohol citrate) | 7.0% |
| | Cetiol V (decyl oleate) | 6.0% |
| | Beeswax, white | 3.0% |
| | Vaseline, white | 12.0% |
| | 1,3-Diisobutyl-cyclohexane | 6.0% |
| (II) | Glycerol 86% | 5.0% |
| | $MgSO_4 7H_2O$ | 0.3% |
| | Water | 60.7% |

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. In a cosmetic preparation selected from the group consisting of suspensions, gels, emulsions, ointments and pastes comprising cosmetic adjuvants selected from the group consisting of water, preservatives, sequestering agents, perfumes, solvents, opacifiers, thickeners, dyes, pH-modifying additives, plant extracts, and skin care ingredients selected from the group consisting of collagens, fatty acids, fatty acid esters, glycols, glycol ethers, animal oils, plant oils and synthetic oils, wherein the improvement comprises, as a refatting cosmetic oil, from 2% to 25% by weight of at least one 1,3-dialkyl-cyclohexane of the formula

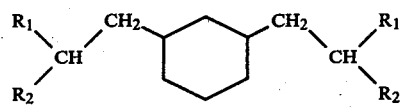

wherein $R_1$ is a member selected from the group consisting of hydrogen and a straight chained or branched $C_1$–$C_{20}$-alkyl and $R_2$ is a straight chained or branched $C_1$–$C_{20}$-alkyl.

2. The cosmetic preparation of claim 1 wherein said amount of said at least one 1,3-dialkyl-cyclohexane in said preparation is from 3% to 25% by weight based on the total weight of said cosmetic product.

3. The cosmetic preparation of claim 1 wherein in said at least one 1,3-dialkyl-cyclohexane, $R_1$ and $R_2$ both represent straight chained or branched $C_1$–$C_6$-alkyl.

4. The cosmetic preparation of claim 1 wherein said at least one 1,3-dialkyl-cyclohexane is 1,3-di(2-ethylhexyl)-cyclohexane.

* * * * *